United States Patent [19]
Gazdag et al.

[11] Patent Number: 5,397,784
[45] Date of Patent: Mar. 14, 1995

[54] STABLE PARENTERAL COMPOSITIONS OF VINBLASTINE OR VINCRISTINE

[75] Inventors: Maria Gazdag; Gabor Szepesi; Takacsi Nagy; Szikla Z. Papp; Laszlo Nagy; Eva E. Kiss; Bobjak M. Zsoldos, all of Budapest, Hungary

[73] Assignee: Richter Gedeon Vegyeszeti Gyar Rt., Budapest, Hungary

[21] Appl. No.: 608,481

[22] Filed: Nov. 2, 1990

[30] Foreign Application Priority Data

Nov. 7, 1989 [HU] Hungary ............... 5804/89

[51] Int. Cl.⁶ ............................. A61K 31/44
[52] U.S. Cl. ................................... 514/283
[58] Field of Search .......................... 514/283

[56] References Cited

U.S. PATENT DOCUMENTS

| | | | |
|---|---|---|---|
| 4,619,935 | 10/1986 | Robison | 514/281 |
| 4,684,638 | 8/1987 | Nagy et al. | 514/185 |
| 4,883,805 | 11/1989 | Kasan et al. | 514/411 |
| 4,923,876 | 5/1990 | Francis et al. | 514/283 |

FOREIGN PATENT DOCUMENTS

0243278 10/1987 European Pat. Off. ....... A61K 9/08

OTHER PUBLICATIONS

Black et al., *J. Pharm. Sci.* 77(7):630–634, Jul. 1988. Studies on the stability of vinblastine sulfate in aqueous solution.
*Chemical Abstracts* 100(16):126905a, 1984, Eli Lily & Co. Aqueous Vinca alkaloid formulations.
*Chemical Abstracts*, 108(24):210210t, 1988. Leverd et al. Stable aqueous solution of vincristine sulfate.
*Chemical Abstracts* 108(10):83040k, 1988, Burger et al. Calcium-, Magnesium- and zinc-ion coordination of vincristine.

*Primary Examiner*—Raymond J. Henley, III
*Assistant Examiner*—T. J. Criares
*Attorney, Agent, or Firm*—Keil & Weinkauf

[57] ABSTRACT

The invention relates to novel, parenterally useful, stable aqueous pharmaceutical compositions, mainly injectable solutions containing a bis-indole alkaloid. The compositions contain the zinc complex of a bis-indole alkaloid, preferably vincristine, vinblastine or 5′-nor-dihydrovinblastine together with a bivalent metal gluconate and a preserving agent dissolved in a mono- or polyhydric alcohol.

The invention further relates to a process for the preparation of the above compositions.

The composition according to the invention can be utilized for the parenteral administration of bis-indole alkaloids in the cancer chemotherapy.

9 Claims, No Drawings

STABLE PARENTERAL COMPOSITIONS OF VINBLASTINE OR VINCRISTINE

The invention relates to novel, parenterally useful stable aqueous pharmaceutical compositions, preferably injectable solutions containing the zinc complex of bis-indole alkaloids, preferably vincristine (hereinafter: VCR), vinblastine (hereinafter: VBL) and 5'-nor-anhydrovinblastine (hereinafter: 5'-nor-VBL). The invention further relates to a process for preparing these compositions by using preservatives.

It is known that bis-indole compounds (alkaloids), and out of these particularly VCR and VBL of natural origin as well as recently the synthetically prepared 5'-nor-VBL play an outstanding role in the antitumour therapy. These compounds were commercialized or described, respectively in the various pharmacopoeias as salts (mainly as sulfates or difumarates, respectively).

It is also known that the injectable dosage form of the above active agents possesses a decisive role in the battle against cancer. Thus, the research and development of various injectable pharmaceutical forms came into prominence in the 80'-s. In this field the injectable formulation described in the U.S. Pat. No. 4,619,935 has to be emphasized, the authors of which broke with the lyophilization techniques used earlier and formulated the composition to be sucked into the syringe in an aqueous solution in one-ampoule form.

The principle of the solution described in the above specification comprises dissolving VCR or, in later publications (see e.g. the Hungarian patent specification No. 191,538) VBL or vindesine in water in the form of their sulfate salts in the presence of an acetate buffer system and then introducing to the solution a microbiological stabilizing agent required for achieving a stable oncological composition. The earlier well-known methyl or propyl 4-hydroxybenzoate were used as stabilizers. An important element of said solution consisted therein that the aqueous solution contained mannitol in a relatively high concentration (100 mg/ml).

However, only a few data indicating a real stability are found among the data involving a recognition of undoubtfully pioneering character. In the Hungarian patent specification mentioned above it has only been published that 94–99% of the original concentration of the VCR sulfate injectable solution was retained after a storage at 5° C. for 9 months, whereas a stability of 98,7–100% after 12 months was published by the authors in the case of VBL.

Although a stability of 94% after 9 months cannot be considered to be sufficient, the above solution had also an other disadvantage since the injectable solutions contained a relatively high number of components. It is well known that it is continuously aimed to introduce to the injectable composition only the most necessary additives and only in the possibly lowest amounts in addition to the active ingredient.

Because of the above disadvantages, further and more preferred solutions were searched. Such a solution has been reported e.g. in the Hungarian patent specification No. 195,513. The authors of this specification, abundantly supported by stability data, found that aqueous solutions of bis-indole compounds could excellently be stabilized by forming the complexes of the bis-indoles with some bivalent metals, mainly zinc ($Zn^{2+}$), calcium ($Ca^{2+}$) or magnesium ($Mg^{2+}$), respectively in the aqueous solution. The existence of the complexes was proven by polarographic examinations. The product obtained as a result of this really persuasive work proved to be sufficiently stable but showed the disadvantage that it consisted of a high number of components: e.g. the product of Example 1 contained 8 components in addition to the active ingredient. Namely, a buffer system consisting of acetic acid and sodium acetate and, similarly to the earlier solution, a relatively high concentration of mannitol were also required in addition to the preservatives.

The product published in the European patent specification No. 0,243,278 also proved to be disadvantageous from the same point of view. According to this latter specification 0.1–2.2% by mass of glycine, a buffer system containing phosphate ions and preservatives (in some cases even 6 components) were used for the preparation of stable injectable solutions of the bis-indoles. In addition to the use of a high number of additives, the stability characteristics of the product were also insufficient. According to the specification the solution remained stable at a pH value of 4.15 ever for 2 years; however, according to our own repeated measurements the product contained the undecomposed active ingredient in an amount of only 93–93.5% after a storage for 6 months.

Thus, the aim of the present invention is to develop a pharmaceutical composition and a process for preparing same, which is more stable than the formulations known up to the present and simultaneously contains a lowest number and minimum concentration of additives according to the up-to-date demands.

The present invention is based on the recognition that, among the metal complexes of bis-indoles, the zinc complex shows the most preferred stability properties; therefore, our developing work has been based on this fact.

Surprisingly, it has been found that the mannitol content, occurring with a high value (about 100 mg/ml) in the earlier solutions in every case, could not only be diminished but also completely omitted. Namely, it has been stated that, surprisingly, an extraordinarily stable aqueous injectable solution requiring no particular buffer system or mannitol could be prepared by portionwise adding gluconates of certain bivalent metals to the above-mentioned alkaloid-zinc complex in aqueous solution.

Thus, the invention relates to a parenterally useful pharmaceutical composition containing bis-indole alkaloid, which comprises zinc complex of the bis-indole alkaloid salt, bivalent metal gluconate and preserving agent dissolved in mono- or polyhydric alcohol in an aqueous solution.

The composition according to the invention contains:
vincristine, vinblastine or 5'-nor-anhydrovinblastine as a bis-indole alkaloid;
calcium, zinc or magnesium gluconate as gluconate of bivalent metal;
methyl and/or propyl 4-hydroxybenzoate as preserving agent; and
ethanol, n-propanol, isopropanol or ethylene glycol as mono- or polyhydric alcohol.

According to an other aspect of the invention, there is provided a process for the preparation of a pharmaceutical composition containing a bis-indole alkaloid, which comprises dissolving a bis-indole alkaloid salt in water, mixing it with an aqueous solution of zinc sulfate, then treating the alkaloid-zinc complex thus obtained with an aqueous solution of the bivalent metal gluconate and supplementing the resulting aqueous solution by adding a preserving agent dissolved in a monohydric or polyhydric alcohol.

In the process according to the invention:
- vincristine sulfate, vinblastine sulfate or 5'-nor-anhydrovinblastine are used as bis-indole alkaloid salts;
- calcium or magnesium or zinc gluconate are used as bivalent metal gluconates;
- ethanol, n-propanol, isopropanol or ethylene glycol are used as mono- or polyhydric alcohols; and
- methyl and/or propyl 4-hdroxybenzoate are used as preserving agents.

According to a preferred embodiment of the process of the invention, an aqueous solution containing VCR-zinc complex is prepared from a VCR sulfate solution of 1.0–1.5 mg/ml concentration with zinc sulfate solution, then a bivalent metal gluconate, preferably zinc, magnesium or calcium gluconate is added up to a concentration of 1.5–2 mg/ml to the above solution.

According to the process of the invention, stable aqueous solutions containing VBL-zinc or 5'-nor-VBL-zinc complex can similarly be prepared as described above.

The most important advantage of the process according to the invention consists therein that it is suitable for the preparation of a parenterally useful composition containing bis-indole active ingredient and possessing a stability lasting for at least 24 months, in the presence of a little amount of additives by using a simple technological procedure.

The stability data were determined as described hereinafter.

The stability of the injectable solutions containing bis-indole active ingredients prepared according to the Examples were controlled by high pressure liquid chromatography (HPLC) method (see: Pharmacopoea of the USA, Ed. XXI, page 1118). The HPLC method was used also in the cases of vinblastine salt solutions (see Pharmacopoea of the USA, Ed. XXI. Suppl. 3, page 2453).

In the case of VCR the HPLC method was accomplished by using a column (250×4.6 mm) packed with Nucleosil 5 μ $C_8$ at a flow rate of 2.0 ml/min at a wavelength of 297 nm. The elution was carried out with a mixture of methanol, water and diethylamine (pH 7.5). The retention time was found to be about 7.0 minutes.

The active ingredient content was determined against an external standard, i.e. a pure aqueous solution having a concentration identical to that of the injectable solution of vincristine sulfate of the same origin as that used in the solution to be determined.

The invention is illustrated in detail by the following non-limiting Examples.

| Components: | g |
| --- | --- |
| VCR sulfate | 0.1000 |
| Methyl 4-hydroxybenzoate | 0.1300 |
| Propyl 4-hydroxybenzoate | 0.0200 |
| Zinc sulfate heptahydrate | 0.0375 |
| Calcium gluconate monohydrate | 0.1900 |
| Ethanol (96%) | 5.0000 |
| Distilled water for injection | up to 100 ml | are weighed in, then filtered to bacterium-free under aseptic conditions and distributed in 100 sterile ampoules.

The composition is prepared as follows.

The above quantity of VCR sulfate is dissolved in 40 ml of water and zinc sulfate dissolved in 5 ml of water is added. The zinc complex thus obtained is mixed with calcium gluconate dissolved in 30 ml of water and the separately prepared ethanolic solution of the 4-hydroxybenzoate(s) is added to the above solution. The solution obtained is filled up to 100 ml and distributed in ampoules under aseptic conditions.

EXAMPLE 2

| Components: | g |
| --- | --- |
| VBL sulfate | 0.1000 |
| Methyl 4-hydroxybenzoate | 0.1300 |
| Propyl 4-hydroxybenzoate | 0.0200 |
| Zinc sulfate heptahydrate | 0.0375 |
| Calcium gluconate monohydrate | 0.1900 |
| Ethanol (96%) | 5.000 |
| Distilled water for injection | up to 100 ml | are weighed in, then filtered to bacterium-free under aseptic conditions and distributed in 20 sterile ampoules of 5 ml volume each.

The injectable solution is prepared as described in Example 1.

EXAMPLE 3

| Components | g |
| --- | --- |
| 5'-nor-VBL ditartrate | 0.5000 |
| Methyl 4-hydroxybenzoate | 0.1300 |
| Propyl 4-hydroxybenzoate | 0.0200 |
| Zinc sulfate heptahydrate | 0.0400 |
| Calcium gluconate monohydrate | 0.2000 |
| Ethanol | 5.0000 |
| Distilled water for injection | up to 100 ml. |

The injectable solution is prepared as described in Example 1.

EXAMPLE 4

Example 1 is followed, except that 0.1500 g of magnesium gluconate is used instead of 0.1900 g of calcium gluconate.

EXAMPLE 5

Example 1 is followed, except that 0.2500 g of zinc gluconate is used instead of 0.1900 g of calcium gluconate.

EXAMPLE 6

Example 1 is followed, except that 100 ml of sterile solution obtained are distributed in 50 ampoules of 2 ml volume each to obtain ampoules containing 2 mg/2 ml of VCR active ingredient each.

EXAMPLE 7

Example 1 is followed, except that instead of VCR sulfate VBL sulfate and instead of ethanol isopropanol are used.

EXAMPLE 8

Example 7 is followed, except that ethylene glycol is used instead of isopropanol.

| Stability tests on the formulation described in Example 1 | | | | |
|---|---|---|---|---|
| Manner and time of storage | Active ingredient content as % of the starting concentration | Impurities | | |
| | | Total | N-Deformyl-VCR | Others |
| 0 | 100,00 | 1,48 | 0,33 | <2 |
| Refrigerator 6 months | 97,80 | 2,82 | 1,29 | <2 |
| Refrigerator 9 months | 97,20 | 2,60 | 1,51 | <2 |
| Refrigerator 12 months | 96,80 | 3,12 | 1,81 | <2 |
| Room temperature, 3 months (protected from light) | 93,10 | 5,43 | 3,04 | <2 |
| Room temperature, 3 months (diffuse light) | 89,40 | 6,85 | 3,17 | >2 |
| 3 months at 40° C. | 80,90 | 12,40 | 7,12 | >2 |
| 3 months at 50° C. | 53,40 | 27,4 | 15,6 | >2 |

| Stability tests on the formulation described in Example 2 | | |
|---|---|---|
| Manner and time of storage | Active ingredient content as % of the starting concentration | Impurities Total |
| 0 | 100,00 | 1,27 |
| refrigerator, 6 months | 100,80 | 1,25 |
| refrigerator, 9 months | 98,5 | 1,22 |
| refrigerator, 12 months | 97,3 | 1,50 |
| refrigerator, 24 months | 97,1 | 1,62 |
| Room temperature 3 months | 98,8 | 1,82 |
| Room temperature 6 months | 95,8 | 2,36 |
| Room temperature 12 months | 95,5 | 2,48 |
| Room temperature 3 months (diffuse light) | 99,0 | 2,05 |
| 3 months at 40° C. | 92,7 | 5,12 |
| 3 months at 50° C. | 69,7 | 15,60 |

We claim:

1. A parenteral composition consisting essentially of a zinc complex of a vincristine or vinblastine, water as a carrier, a stabilizing amount of a bivalent metal gluconate and a preserving amount of a preserving agent dissolved in a mono- or polyhydric alcohol.

2. The composition of claim 1 wherein the bivalent metal gluconate is calcium, zinc or magnesium gluconate.

3. The composition of claim 1 wherein the preserving agent is methyl 4-hydroxybenzoate or propyl 4-hydroxybenzoate.

4. The composition of claim 1 wherein the alcohol is ethanol, n-propanol, isopropanol or ethylene glycol.

5. A process for the stabilization of a parenterally useful composition consisting essentially of a zinc complex of a bis-indole alkaloid complex, water, a bivalent metal gluconate stabilizing agent, and a preserving agent dissolved in a mono- or polyhdric alcohol, said process consisting essentially of dissolving a bis-indole alkaloid salt in water to form a first solution, mixing the first solution with an aqueous solution of zinc sulfate to form a second solution, which consists essentially of the alkaloid-zinc complex, mixing the second solution with an aqueous solution with a preserving agent dissolved in a mono- or polyhydric alcohol to form the stabilized aqueous parenteral complex solution of vincristine or vinblastine.

6. A process as claimed in claim 5, which comprises using vincristine sulfate or vinblastine sulfate as the vincristine or vinblastine salt.

7. A process as claimed in claim 5, which comprises using calcium, magnesium or zinc gluconate as the bivalent metal gluconate.

8. A process as claimed in claim5, which comprises using ethanol, n-propanol, isopropanol or ethylene glycol as mono- or polyhydric alcohol.

9. A process as claimed in claim 5, which comprises using methyl 4-hydroxybenzoate and/or propyl 4-hydroxybenzoate as preserving agent.

* * * * *